United States Patent
Nakamura et al.

(10) Patent No.: US 9,198,804 B2
(45) Date of Patent: Dec. 1, 2015

(54) METHOD OF MANUFACTURING SHEET, METHOD OF MANUFACTURING MATERIAL OF ABSORBENT ARTICLE, AND APPARATUS TO MANUFACTURE SHEET

(75) Inventors: Taishi Nakamura, Kagawa (JP); Shinichi Ishikawa, Kagawa (JP); Yukihisa Akano, Kagawa (JP); Satoshi Mitsuno, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 1024 days.

(21) Appl. No.: 13/262,718

(22) PCT Filed: Mar. 10, 2010

(86) PCT No.: PCT/JP2010/054038
§ 371 (c)(1),
(2), (4) Date: Dec. 9, 2011

(87) PCT Pub. No.: WO2010/113609
PCT Pub. Date: Oct. 7, 2010

(65) Prior Publication Data
US 2012/0086145 A1    Apr. 12, 2012

(30) Foreign Application Priority Data
Apr. 3, 2009 (JP) ................................. 2009-091503

(51) Int. Cl.
*A61F 13/15* (2006.01)
*B29C 53/22* (2006.01)
(Continued)

(52) U.S. Cl.
CPC ..... *A61F 13/15593* (2013.01); *A61F 13/15699* (2013.01); *A61F 13/15731* (2013.01);
(Continued)

(58) Field of Classification Search
None
See application file for complete search history.

(56) References Cited

U.S. PATENT DOCUMENTS 3,985,600 A * 10/1976 Blais ............................. 156/229
7,803,244 B2 * 9/2010 Siqueira et al. ............... 156/229
(Continued)

FOREIGN PATENT DOCUMENTS

| CN | 1620533 A | 5/2005 |
| JP | 2274250 A | 11/1990 |

(Continued)

OTHER PUBLICATIONS

Office Action mailed Sep. 29, 2013, corresponds to Chinese patent application No. 201080021401.5.
(Continued)

*Primary Examiner* — Jeffrey Wollschlager
(74) *Attorney, Agent, or Firm* — Hauptman Ham, LLP

(57) ABSTRACT

A method of manufacturing a sheet includes: rotating in a circumferential direction, a first roll having a protruding portion group, and a second roll opposing the first roll and having a region with the different flexibility property; and sandwiching the sheet with the protruding portion group and the outer circumferential face of the second roll. The protruding portion group has a plurality of rows of protruding portion rows with intervals therebetween in the circumferential direction. Each of the protruding portion rows includes a plurality of protruding portions aligned along a rotational axis direction of the first roll. A position of a downstream end in the circumferential direction of at least one protruding portion of the protruding portions positioned most downstream of the protruding portion group in the circumferential direction is arranged shifted from a position of a downstream end of another protruding portion configuring the protruding portion row.

12 Claims, 13 Drawing Sheets

(51) Int. Cl.
| | |
|---|---|
| *B29C 43/24* | (2006.01) |
| *A61F 13/49* | (2006.01) |
| *A61F 13/515* | (2006.01) |
| *B29C 59/04* | (2006.01) |
| *B29C 53/26* | (2006.01) |
| *B29C 44/56* | (2006.01) |
| *B29C 53/28* | (2006.01) |
| *B29C 43/46* | (2006.01) |
| *B29C 43/22* | (2006.01) |
| *B29C 59/02* | (2006.01) |

(52) U.S. Cl.
CPC ..... *A61F13/15739* (2013.01); *A61F 13/15756* (2013.01); *A61F 13/49011* (2013.01); *A61F 13/515* (2013.01); *B29C 43/226* (2013.01); *B29C 44/5627* (2013.01); *B29C 53/265* (2013.01); *B29C 53/285* (2013.01); *B29C 59/02* (2013.01); *B29C 59/04* (2013.01); *B29C 2043/463* (2013.01); *B29C 2043/464* (2013.01)

(56) References Cited

U.S. PATENT DOCUMENTS

| | | | |
|---|---|---|---|
| 2002/0022427 A1* | 2/2002 | Curro et al. | 442/373 |
| 2003/0028165 A1* | 2/2003 | Curro et al. | 604/378 |
| 2004/0133180 A1* | 7/2004 | Mori et al. | 604/385.25 |
| 2004/0224136 A1* | 11/2004 | Collier et al. | 428/196 |
| 2004/0230171 A1* | 11/2004 | Ando et al. | 604/355 |
| 2005/0004547 A1* | 1/2005 | Lavash | 604/385.16 |
| 2005/0064136 A1* | 3/2005 | Turner et al. | 428/131 |
| 2006/0047257 A1* | 3/2006 | Raidel et al. | 604/383 |
| 2006/0243367 A1* | 11/2006 | Engelhart et al. | 156/62.6 |
| 2007/0093157 A1* | 4/2007 | Shannon et al. | 442/59 |
| 2007/0129699 A1* | 6/2007 | Ohtsuka et al. | 604/380 |
| 2007/0135787 A1* | 6/2007 | Raidel et al. | 604/383 |
| 2008/0028902 A1* | 2/2008 | Baggot et al. | 83/13 |
| 2008/0280088 A1* | 11/2008 | Baum | 428/43 |
| 2009/0137977 A1* | 5/2009 | Fukae et al. | 604/378 |

FOREIGN PATENT DOCUMENTS

| | | |
|---|---|---|
| JP | 2003275238 A | 9/2003 |
| JP | 2008055198 A | 3/2008 |
| WO | 03071019 A1 | 8/2003 |

OTHER PUBLICATIONS

Chinese Office Action with Search Report for Application No. 201080021401.5 dated Mar. 4, 2013.
International Search Report for PCT/JP2010/054038 dated May 25, 2010..
Office Action as issued in corresponding Japanese Patent Application No. 2009-091503.
Office Action issued on Jul. 17, 2013 corresponds to Eurasian patent application No. 201101444/31.
Office Action issued Dec. 18, 2013, corresponds to Ukrainian patent application No. a201112616/M.
Supplementary European Search Report issued Jan. 9, 2014, corresponds to European patent application No. 10758385.8.
Office Action dated Apr. 24, 2015, corresponding to Vietnamese patent application No. 1-2011-02490.

* cited by examiner

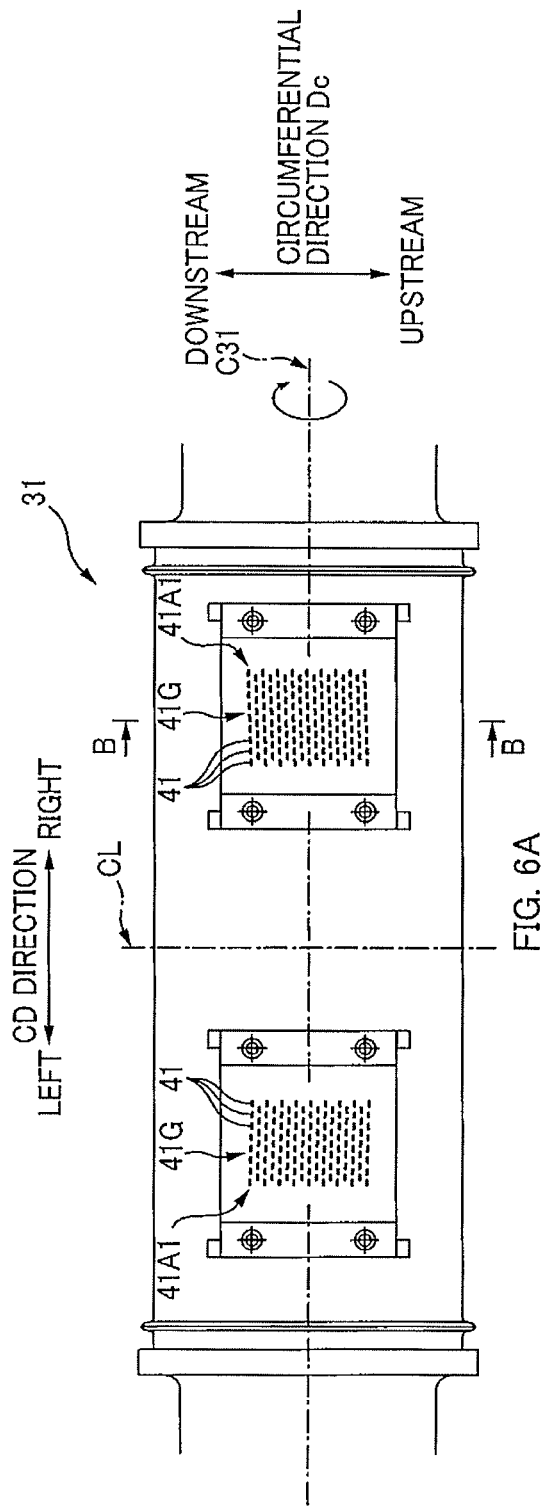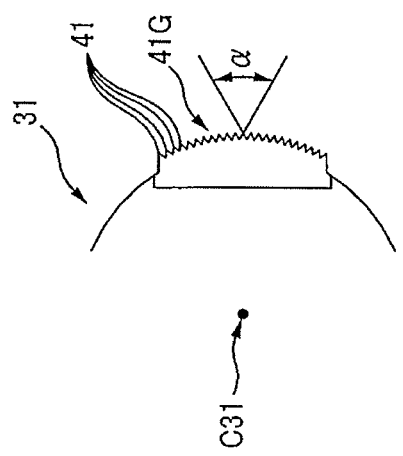

METHOD OF MANUFACTURING SHEET, METHOD OF MANUFACTURING MATERIAL OF ABSORBENT ARTICLE, AND APPARATUS TO MANUFACTURE SHEET

RELATED APPLICATIONS

The present application is a National Phase of International Application Number PCT/JP2010/054038, filed Mar. 10, 2010 and claims priority from, Japanese Application No. 2009-091503, filed Apr. 3, 2009.

TECHNICAL FIELD

The present invention relates to methods of manufacturing a sheet configuring an absorbent article, methods of manufacturing a material of the absorbent article, and apparatuses to manufacture a sheet.

BACKGROUND ART

As an example of an absorbent article that absorbs a bodily waste fluid, a disposable diaper is used. This disposable diaper includes an absorbent main body that is applied to a crotch part of a wearer and absorbs a bodily waste fluid, an abdominal side member joined to one end portion in a longitudinal direction of an absorbent main body to cover an abdominal side portion of the wearer, and a back side member joined to another end portion in the longitudinal direction of the absorbent main body to cover a back side portion of the wearer.

Then, usually, as these back side member and abdominal side member, a sheet like member having flexibility to appropriately fasten tightly around the waist of the wearer is used. For example as shown in a perspective view in FIG. 1, this sheet like member 81 is formed by such as laying on and fixing a plurality of elastic members 85 such as a rubber thread along a width direction of the diaper onto an appropriate sheet 83 such as a nonwoven fabric.

In a region 81a to which an end portion of an absorbent main body is to be joined in the sheet like member 81, however, the elastic member 85 is divided in order to weaken elasticity of the sheet like member 81. This is because, if elasticity of this region 81a is strong, creases appear in the end portion of the absorbent main body by contraction of the region 81a, and liquid absorbency of the absorbent main body deteriorates.

Then, regarding this dividing method, PTL1 discloses dividing the elastic member 85 with embossing rolls 91, 93 that rotate in a circumferential direction Dc (refer to FIG. 1). Namely, in a predetermined area on an outer circumferential face of the top roll is provided an embossing protruding portion group 92G corresponding to the region 81a. Then, when passing the sheet 81 in between the rotating top roll 91 and the bottom roll 93, by compressing the elastic member 85 of the region 81a with embossing protruding portions 92 of the embossing protruding portion group 92G and the outer circumferential face of the bottom roll 93, the elastic member 85 is divided, and elasticity of the region 81a is weakened.

CITATION LIST

Patent Literature

PTL1: JP-A-2008-55198

SUMMARY

Technical Problem

With the alignment of the embossing protruding portions 92 of the embossing protruding portion group 92G however, poor division of the elastic member 85 may occur in part. For example, in the case where an arrangement direction of the embossing protruding portions 92 of the embossing protruding portion group 92G are aligned in parallel to a rotational axis direction C91 of the top roll 91 as shown in FIG. 1, a counterforce of a dividing load for the one row load acts all together on the top and bottom rolls 91, 93. Then, the top roll 91 rises upward for an instance due to this large counterforce, and the part of the embossing protruding portion 92 corresponding to the rising timing cannot effectively perform dividing. As a result, there is a possibility that elasticity of the region 81a remains large in part. Then, such a rising phenomenon is particularly likely to occur when starting dividing, namely when dividing with the embossing protruding portion row 92A configuring a downstream end edge in the circumferential direction Dc of the embossing protruding portion group 92G.

Further, the top and bottom rolls 91, 93 are generally stored inside a case like housing (not shown), and from the housing, a total load in a vertical direction that is necessary when sandwiching is added. Then, normally, the total load is a constant value. In this case, if the arrangement direction of the embossing protruding portions 92, 92 ... are in parallel with the rotational axis direction C91 of the top roll 91, a plurality of embossing protruding portions 92, 92 ... arranged in a line in the rotational axis direction C91 simultaneously divide the elastic member 85, thus of the total load the load to be assigned for one embossing protruding portion 92 becomes small. Then, for that amount, it becomes difficult for the elastic member 85 to be divided, and as a result, elasticity of the region 81a remains large in part.

The invention has been made in view of the above problems, and the object is to provide a method of manufacturing a sheet in which in a predetermined portion of the sheet a region having a different flexibility property can be certainly formed, a method of manufacturing a material of an absorbent article, and an apparatus to manufacture a sheet.

Solution to Problem

An aspect of the invention to achieve the above advantages is a method of manufacturing a sheet formed, in a predetermined portion of the sheet, with a region having a different flexibility property, the sheet configuring an absorbent article, the method including:

rotating in a circumferential direction both a first roll formed with a protruding portion group in a predetermined area of an outer circumferential face and a second roll arranged with an outer circumferential face opposing the first roll, forming, in the sheet, a region with the different flexibility property by passing the sheet in between the first roll and the second roll, and sandwiching the sheet with the protruding portion group and the outer circumferential face of the second roll, wherein the protruding portion group has a plurality of rows of protruding portion rows with intervals therebetween in the circumferential direction, each of the protruding portion rows including a plurality of protruding portions aligned along a rotational axis direction of the first roll, wherein a position of a downstream end in the circumferential direction of at least one protruding portion of the protruding portions configuring the protruding portion row positioned most downstream of the protruding portion group in the circumferential direction is arranged shifted from a position of a downstream end of another protruding portion configuring the protruding portion row.

Another aspect is a manufacturing apparatus of a sheet formed in a predetermined portion of the sheet with a region having a different flexibility property, the sheet configuring an absorbent article, the apparatus including:

a first roll that rotates in a circumferential direction and that is formed with a protruding portion group in a predetermined area of an outer circumferential face, a second roll that rotates in the circumferential direction and that is arranged with an outer circumferential face opposing the first roll, wherein forming, in the sheet, a region with the different flexibility property by passing a sheet in between the first roll and the second roll, and by sandwiching the sheet between the protruding portion group and the outer circumferential face of the second roll, wherein the protruding portion group has a plurality of protruding portion rows with intervals therebetween in the circumferential direction, each of the protruding portion rows including a plurality of protruding portions aligned along a rotational axis direction of the first roll, wherein a position of a downstream end in the circumferential direction of at least one protruding portion of the protruding portions configuring the protruding portion row positioned most downstream of the protruding portion group in the circumferential direction is arranged shifted from a position of a downstream end of another protruding portion configuring the protruding portion row.

Advantageous Effects of Invention

In accordance with the invention, in a predetermined portion of a sheet a region with a different flexibility property from the sheet can be certainly formed.

BRIEF DESCRIPTION OF DRAWINGS

FIG. 1 is an explanatory diagram of a known method to selectively weaken elasticity added to a sheet 81 in a part of a region 81a.

FIG. 6A is explanatory diagram of an arrangement pattern of a slit blade 41 in slit blade groups 41G, 41G and is a front view showing an appearance of a top roll 31, and FIG. 6B is a B-B cross section view in FIG. 6A.

DESCRIPTION OF EMBODIMENTS

Figure 1:
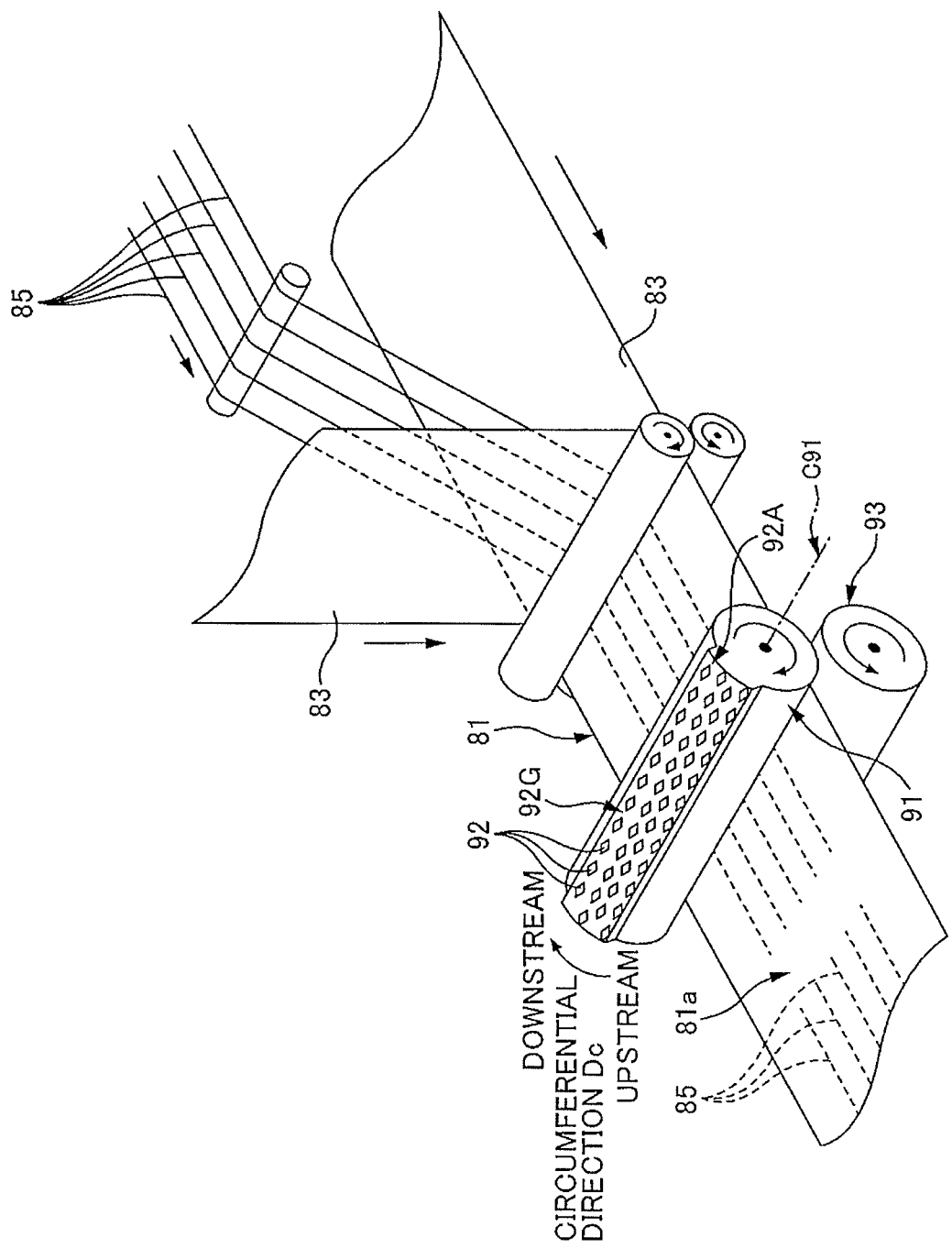

From the description in this specification and attached drawings, at least the below matters will become clear.

A method of manufacturing a sheet formed, in a predetermined portion of the sheet, with a region having a different flexibility property, the sheet configuring an absorbent article, the method including:

rotating in a circumferential direction both a first roll formed with a protruding portion group in a predetermined area of an outer circumferential face and a second roll arranged with an outer circumferential face opposing the first roll, forming, in the sheet, a region with the different flexibility property by passing the sheet in between the first roll and the second roll, and sandwiching the sheet with the protruding portion group and the outer circumferential face of the second roll, wherein the protruding portion group has a plurality of rows of protruding portion rows with intervals therebetween in the circumferential direction, each of the protruding portion rows including a plurality of protruding portions aligned along a rotational axis direction of the first roll, wherein a position of a downstream end in the circumferential direction of at least one protruding portion of the protruding portions configuring the protruding portion row positioned most downstream of the protruding portion group in the circumferential direction is arranged shifted from a position of a downstream end of another protruding portion configuring the protruding portion row.

In accordance with such a method of manufacturing a sheet, a position of a downstream end of at least one protruding portion belonging to the protruding portion row positioned most downstream is arranged shifted in the circumferential direction than other protruding portion in the protruding portion row. Thus, a sandwiching timing of the protruding portion shifted in the position of the downstream end is shifted in respect to the other protruding portion, and a counterforce that acts on the first roll and the second roll when sandwiching the sheet with the protruding portion row positioned most downstream is alleviated for the shifted amount in the timing as above-described. Therefore, the rising of the roll is suppressed. Then, with suppressing of the rising, the sheet can be certainly sandwiched with a larger number of protruding portions, and as a result the region with the different flexibility property can be certainly formed.

Further, when sandwiching the sheet, even in the case where only a constant total load can be added to the roll, for just the protruding portion amount that is arranged with the position of the downstream end in the circumferential direction shifted, a load to be assigned for one protruding portion can be expanded. As a result, the sandwiching force of the protruding portion can be made large, and the region with the different flexibility property can be certainly formed.

With the method of manufacturing of a sheet, wherein preferably the position of the downstream end in the circumferential direction of the protruding portion belonging to the protruding portion row positioned most downstream is subsequently shifted to an upstream side in the circumferential direction, as the position advances in one direction of the rotational axis direction.

In accordance with such a method of manufacturing a sheet, the sandwiching timing of the sheet by the protruding portions belonging to the most downstream protruding portion row can be certainly made different from each other and dispersed, and thus the counterforce that acts on the first roll and the second roll when the protruding portions sandwich the sheet is further alleviated. As a result, the rising of the roll is further suppressed.

Further, with the above-described dispersion of the sandwiching timing, even when only a constant total load can be added to the roll when sandwiching, the load assigned for one protruding portion can be further expanded.

With the method of manufacturing a sheet, wherein preferably extending over all the protruding portion rows of the protruding portion group, the position of the downstream end in the circumferential direction of the protruding portion belonging to each protruding portion row is subsequently shifted to the upstream side in the circumferential direction, as the position advances in one direction of the rotational axis direction.

In accordance with such a method of manufacturing a sheet, extending over all protruding portion rows of the protruding portion group, the sandwiching timing of the sheet with the protruding portions can certainly be made different from each other and dispersed, and thus the counterforce that acts on the first roll and the second roll when the protruding portions sandwich the sheet is furthermore alleviated. Therefore, the rising of the roll can be furthermore certainly suppressed.

Further, with the above-described dispersion of the sandwiching timing, even when only a constant total load can be added to the roll when sandwiching, the load assigned for one protruding portion can be further enlarged.

With the method of manufacturing a sheet, wherein preferably a longitudinal direction of the protruding portion is arranged inclined by only a predetermined angle (excluding 90°) from the rotational axis direction.

In accordance with such a method of manufacturing a sheet, the longitudinal direction of the protruding portion is inclined for only a predetermined angle from the rotational axis direction, thus the sandwiching timing of each section in the longitudinal direction between the protruding portions can be dispersed, and thus the counterforce that acts on the first roll and the second roll when the protruding portion sandwiches the sheet is alleviated. Thus, the rising of the roll is furthermore certainly suppressed.

With the method of manufacturing a sheet, wherein preferably extending over all the protruding portion rows of the protruding portion group, the protruding portions belonging to the same protruding portion row are not overlapped with each other in respect to the circumferential direction.

In accordance with such a method of manufacturing a sheet, the protruding portions belonging to the same protruding portion row are not overlapped with each other in respect to the circumferential direction, thus the sandwiching timing of the sheet with the protruding portions belonging to the same protruding portion row can be made different from each other and dispersed, and thus the counterforce that acts on the first roll and the second roll when forming the region can be alleviated. Therefore, the rising of the roll can be furthermore certainly suppressed.

Further, with the dispersion of the above-described sandwiching timing, even in the case where only a constant total load can be added to the roll when sandwiching, the load to be assigned for one protruding portion can be enlarged.

With the method of manufacturing a sheet, wherein preferably the protruding portion rows adjacent to each other in the circumferential direction are not overlapped with each other in respect to the circumferential direction.

In accordance with such a method of manufacturing a sheet, the protruding portion rows adjacent to each other in the circumferential direction are not overlapped with each other in the circumferential direction, thus between the adjacent protruding portion rows, the sandwiching timing of the sheet can be made different from each other and dispersed, and thus the counterforce that acts on the first roll and the second roll when forming the region is alleviated. Therefore, the rising of the roll can be furthermore certainly suppressed.

Further, with the above-described dispersion of the sandwiching timing, even in the case where only a constant total load can be added to the roll when sandwiching, the load to be assigned for one protruding portion can be enlarged.

With the method of manufacturing a sheet, preferably
wherein the protruding portion is a blade member,
wherein a part of the sheet sandwiched between the protruding portion and the outer circumferential face of the second roll is divided in a thickness direction of the sheet.

In accordance with such a method of manufacturing a sheet, the region with a different flexibility property is to be formed with slits that cut through the sheet in the thickness direction, for the number of the protruding portions of the protruding portion group. Then, with theses slits both surfaces of the sheet become an air permeable state. Therefore, the sheet with increased air permeability in the region with a different flexibility property can be manufactured.

With the method of manufacturing a sheet, preferably
wherein a pair of the protruding portion groups is provided in each position sandwiching a center in the rotational axis direction of the outer circumferential face of the first roll,
wherein a protruding portion of one protruding portion group of the pair of protruding portion groups is arranged based on a predetermined arrangement pattern,
wherein a protruding portion of another protruding portion group of the pair of protruding portion groups is arranged based on an arrangement pattern in a mirror image relationship of the arrangement pattern in respect to a center of the rotational axis direction.

In accordance with such a method of manufacturing a sheet, the pair of protruding portion groups are each provided in positions that sandwich the center in the rotational axis direction, and these pair of protruding portion groups are formed so that the protruding portions are arranged based on an arrangement pattern in which the protruding portion groups are in a mirror image relationship with each other. Therefore, the counterforce that acts on the first roll and the second roll when forming the region with the different flexibility property can be made as a substantially symmetric pressure distribution in regard to the center, and as a result an asymmetric load in regard to the center is not placed on the sheet or the roll, and thus the method is superior in view of stability when processing the region.

With the method of manufacturing a sheet,
wherein preferably the protruding portion belonging to one protruding portion group and the protruding portion belonging to the other protruding portion group are not overlapped with each other in respect to the circumferential direction.

In accordance with such a method of manufacturing a sheet, since all the protruding portions belonging to the one protruding portion group and all the protruding portions belonging to the other protruding portion groups are not overlapped in respect to the circumferential direction, between these protruding portion groups the sandwiching timing of the sheet can be made different from each other and dispersed, and thus the counterforce that acts on first roll and second roll when forming the region is alleviated.

Further, with the above-described dispersion of the sandwiching timing, even when only the constant total load can be added to the roll when sandwiching, the load to be assigned to each protruding portion can be enlarged.

A method of manufacturing a material using a sheet manufactured by a method of manufacturing a sheet, wherein the absorbent article includes an absorbent main body that is applied to a crotch portion of a wearer and that absorbs a bodily waste fluid, an abdominal side member joined to one end portion in a longitudinal direction of the absorbent main body to cover an abdominal side portion of the wearer, and a back side member joined to another end portion in the longitudinal direction of the absorbent main body to cover a back side portion of the wearer, wherein the sheet configures at least one of the abdominal side member and the back side member, wherein a region in the sheet with the different flexibility property is made weaker in elasticity than a region other than the relevant region, wherein the region, in the sheet, with the different flexibility property is joined with end portions of the absorbent main body and forms the material.

In accordance with the method of manufacturing a material of an absorbent article, creases in the end portions in the longitudinal direction of the absorbent main body can be effectively prevented, and as a result, an absorbent article superior in liquid absorbency can be manufactured.

With the method of manufacturing a material of an absorbent article, preferably wherein the protruding portion is a blade member, wherein a part of the sheet sandwiched with the protruding portion and the outer circumferential face of the second roll is divided in the thickness direction of the sheet and cut through, wherein the sheet is to be joined to a surface to the wearer's side of the absorbent main body.

In accordance with the method of manufacturing a material of an absorbent article, the region of the sheet to be joined to the end portions in the longitudinal direction of the absorbent main body is formed with the slits cut through in the thickness direction of the sheet for the number of the protruding portions of the protruding portion group, and air permeability of the region is increased by the openings of these slits. Therefore, the absorbent article that can decrease the wearer's skin opposing the end portions in the longitudinal direction of the absorbent main body becoming hot and stuffy and the like can be manufactured.

Further, with a manufacturing apparatus of a sheet formed in a predetermined portion of the sheet with a region having a different flexibility property, the sheet configuring an absorbent article, the apparatus including:

a first roll that rotates in a circumferential direction and that is formed with a protruding portion group in a predetermined area of an outer circumferential face, a second roll that rotates in the circumferential direction and that is arranged with an outer circumferential face opposing the first roll, wherein forming, in the sheet, a region with the different flexibility property by passing a sheet in between the first roll and the second roll, and by sandwiching the sheet between the protruding portion group and the outer circumferential face of the second roll, wherein the protruding portion group has a plurality of protruding portion rows with intervals therebetween in the circumferential direction, each of the protruding portion rows including a plurality of protruding portions aligned along a rotational axis direction of the first roll, wherein a position of a downstream end in the circumferential direction of at least one protruding portion of the protruding portions configuring the protruding portion row positioned most downstream of the protruding portion group in the circumferential direction is arranged shifted from a position of a downstream end of another protruding portion configuring the protruding portion row.

In accordance with such a manufacturing apparatus of the sheet, the position in the downstream end of at least one protruding portion belonging to the protruding portion row positioned most downstream is arranged shifted in the circumferential direction from the other protruding portion of the protruding portion row. Therefore, the sandwiching timing of the protruding portion in which the position of the downstream end is shifted is shifted from that of the other protruding portion, thus the counterforce that acts on the first roll and the second roll when the protruding portion row positioned most downstream sandwiches the sheet is alleviated for the above-described timing shift amount. As a result, the rising of the roll is alleviated. Then, by suppressing this rising, the sheet can be certainly sandwiched with a larger number of protruding portions, and as a result the region with the different flexibility property can be formed in the sheet.

Further, even in the case where only a constant total load can be added to the roll when sandwiching the sheet, for the protruding portion in which the position of the downstream end is arranged shifted in the circumferential direction, the load to be assigned for one protruding portion can be enlarged. As a result, a sandwiching force in the protruding portion can be made large, and the region with the different flexibility property can be certainly formed.

—The Present Embodiment—

A method of manufacturing a sheet and an apparatus to manufacture a sheet of this embodiment are applied to a manufacturing line of, for example, a disposable diaper 1 (corresponds to absorbent article).

Figure 2:
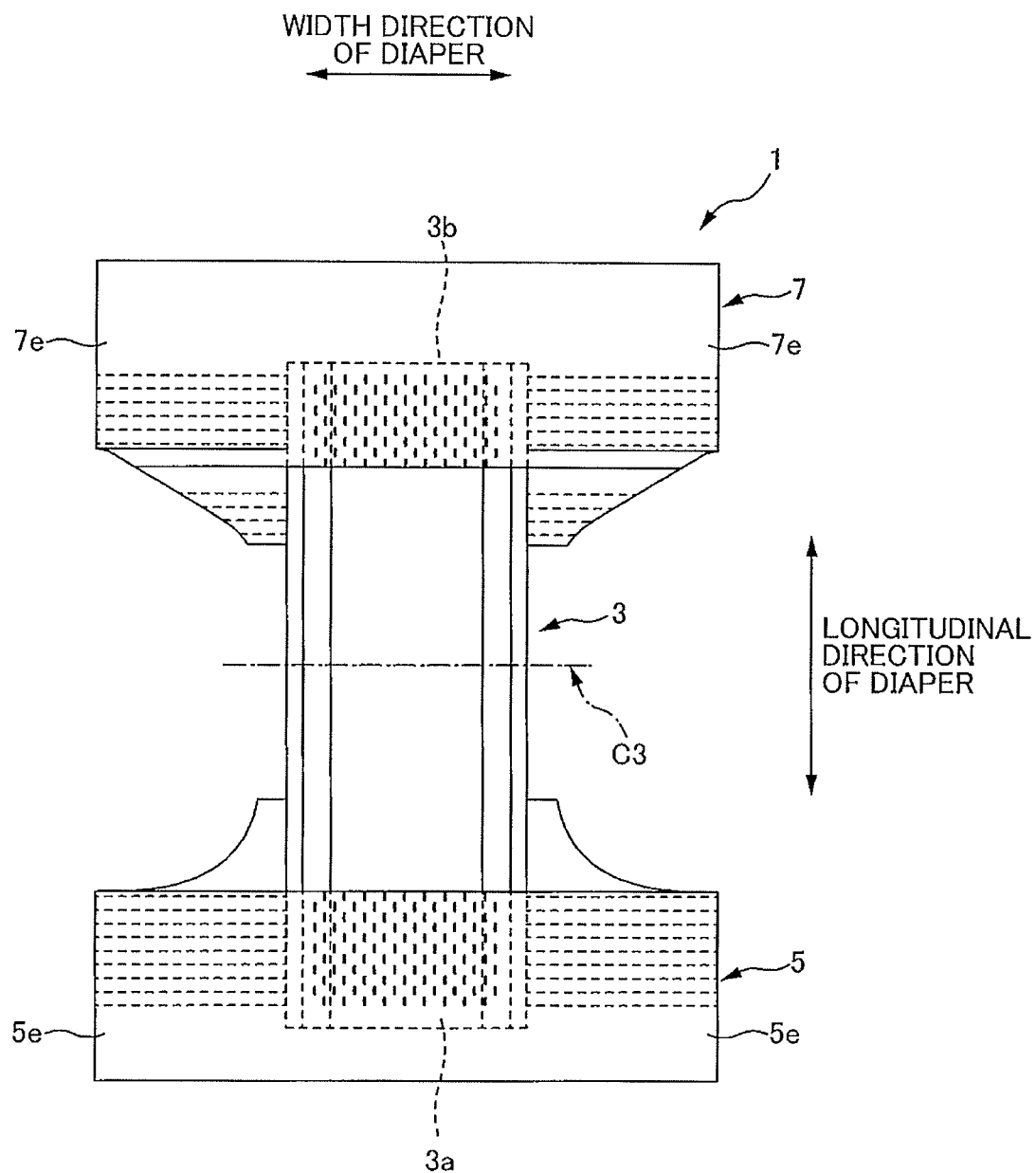
FIG. 2 is a plan view of an opened state of a disposable diaper 1.
Figure 3:
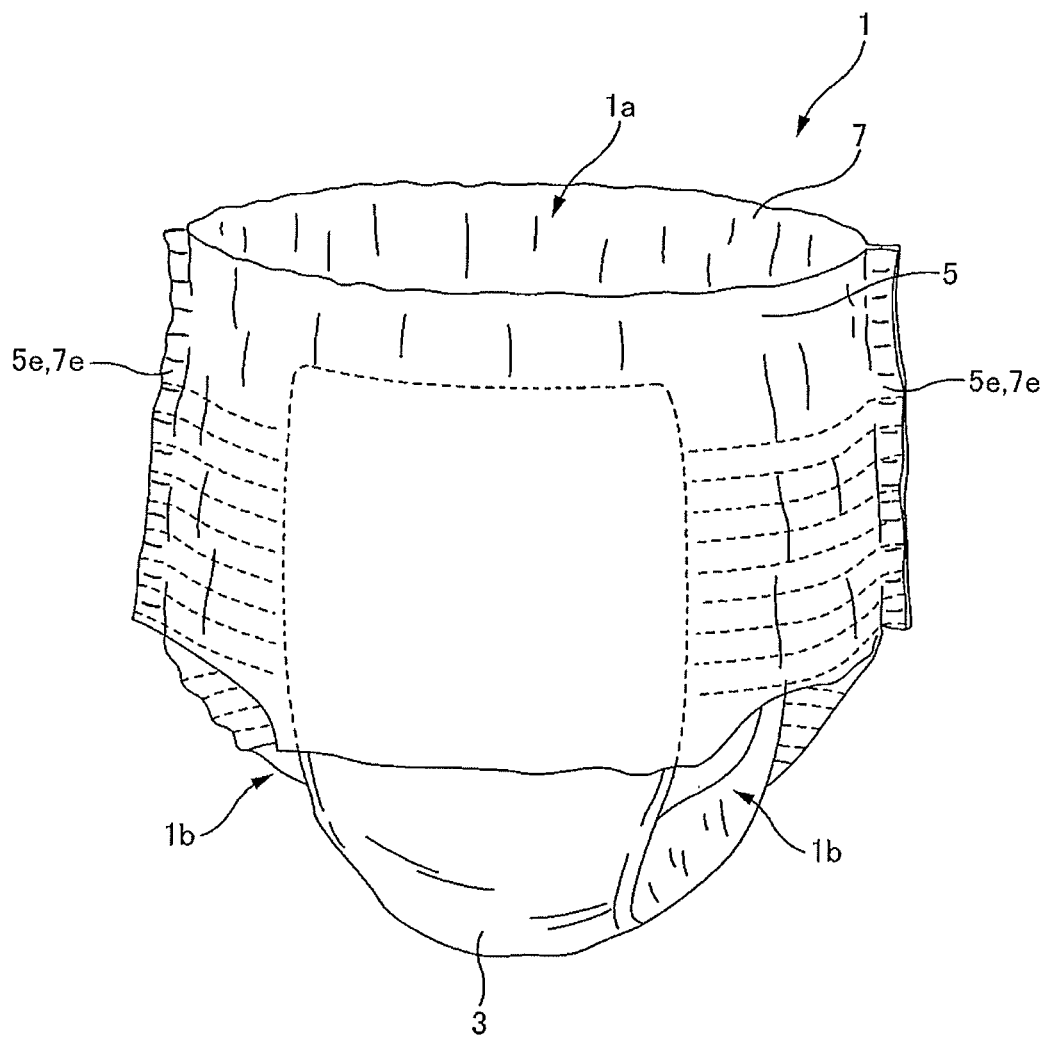
FIG. 3 is a perspective view of a worn state of the diaper.
Figure 4:
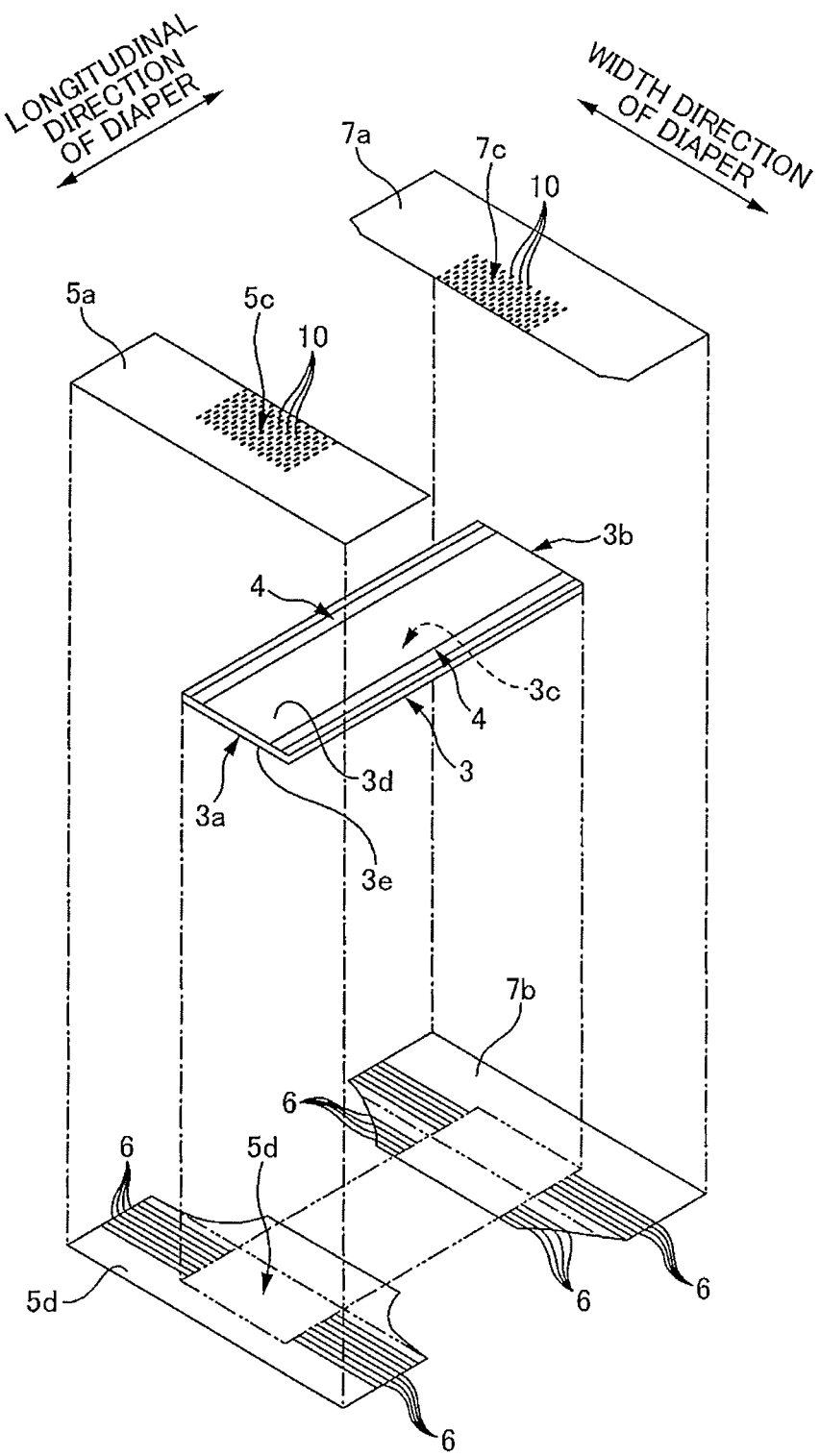
FIG. 4 is an exploded perspective view of the diaper.

FIG. 2 to FIG. 4 are explanatory diagrams of the disposable diaper 1. FIG. 2 is a plan view of an opened state, FIG. 3 is a perspective view of a worn state, and FIG. 4 is an exploded perspective view.

As shown in FIG. 2, the diaper 1 includes an absorbent main body 3 that is applied to a wearer's crotch portion and absorbs a bodily waste fluid, an abdominal side strip member 5 (corresponds to abdominal side member) that has been joined to a front end portion 3a in a longitudinal direction of the absorbent main body 3 so as to cover the wearer's abdominal side portion, and a back side strip member 7 (corresponds to back side member) that has been joined to a back end portion 3b in the longitudinal direction of the absorbent main body 3 so as to cover the wearer's back side portion, and the appearance of the diaper 1 in the open state is a planar substantially H shape. Note that, in this open state, the longitudinal direction of the diaper 1 matches the longitudinal direction of the absorbent main body 3, and further a width direction of the diaper 1 intersects with the longitudinal direction.

Then, from this open state, the diaper 1 is folded into two with a central portion C3 in the longitudinal direction of the absorbent main body 3 as a folding position, and when the strip members 5, 7 opposing each other in this two-folded state are fixed at the wearer's sides in sections to be contacted to each other 5e, 7e, the strip members 5, 7 are connected to each other in a circular state, and thus the diaper 1 in a worn state formed with a waist opening 1a and a pair of around-leg openings 1b, 1b is formed as shown in FIG. 3.

As shown in FIG. 4, the absorbent main body 3 includes an absorbent body 3c made of a liquid absorbent fiber such as a pulp fiber, a liquid permeable surface sheet 3d that covers the absorbent body 3c from the wearer's skin side, and a liquid nonpermeable back face sheet 3e that covers the absorbent body 3c from an opposite side of the surface sheet 3d. The absorbent body 3c may include a superabsorbent polymer. Further, the absorbent main body 3 may include a pair of standing gathers 4, 4 by arranging an elastic member (not shown) such as a rubber thread along both end edges in the width direction.

The abdominal side strip member 5 has a skin side sheet 5a that comes into contact with the wearer's skin and an outer side sheet 5b that is an outer. Then, these sheets 5a, 5b are adhered to each other with such as a hotmelt adhesive in a state the front end portion 3a in the longitudinal direction of the absorbent main body 3 is sandwiched between the sheets 5a, 5b. An elastic member 6 such as a rubber thread in an extended state is fixed along the width direction of the diaper 1 to the outer side sheet 5b, thus flexibility is added in the width direction to the outer side sheet 5b Note that, the elastic member 6 is not arranged in the region 5d where the front end portion 3a is joined to the absorbent main body 3 of the outer side sheet 5b This is because if elasticity in this region 5d is strong, the region 5d largely contracts in the width direction of the diaper 1, and therefore creases appear in the front end portion 3a of the absorbent main body 3 and its liquid absorbent property deteriorates. On the other hand, a flexible sheet added with flexibility by such as a so-called gear drawing processing is used as the skin side sheet 5a Note that, due to a similar reason to the outer side sheet 5b, elasticity of the region 5c to be joined with the front end portion 3a of the absorbent main body 3 is weakened in the width direction of the diaper 1, by putting in multiple slits 10 in this region 5c. In more detail, these slits 10 are cut through in the thickness direction of the skin side sheet 5a, and the longitudinal direction of the slits 10 is facing a direction intersecting the width direction of the diaper 1. Thus, the slits 10 are made so as to be able to open promptly under the effect of a tensile force in the width direction of the diaper 1, and thus elasticity of the region 5c in the width direction is weakened. Note that, with such openings of the slits 10, air permeability of the region 5c is improved and also contributes to prevent stuffiness.

The back side strip member 7 is only different in shape with the abdominal side strip member 5, and its configuration is substantially the same. Namely, the back side strip member 7 also includes a skin side sheet 7a that comes into contact with a skin of the wearer, and an outer side sheet 7b that becomes an outer, and these sheets 7a, 7b are adhered together by such as a hotmelt adhesive in a state sandwiching the back end portion 3b of the absorbent main body 3 in the longitudinal direction between these sheets 7a, 7b The structure of the skin side sheet 7a and the outer side sheet 7b is also the same as in the case of the above-described abdominal side strip member 5. For example, a flexible sheet is used for the skin side sheet 7a, and elasticity of the region 7c that is to be joined with the back end portion 3b of the absorbent main body 3, is weakened in regards to the width direction of the diaper 1 by putting in multiple slits 10 in the region 7c.

Such a diaper 1 is completed by having any component that continuously flows in the manufacturing line as a base material, and by such as joining various components to the base material. A method of manufacturing a sheet and an apparatus 30 to manufacture a sheet of this embodiment handles one step.

Figure 5:
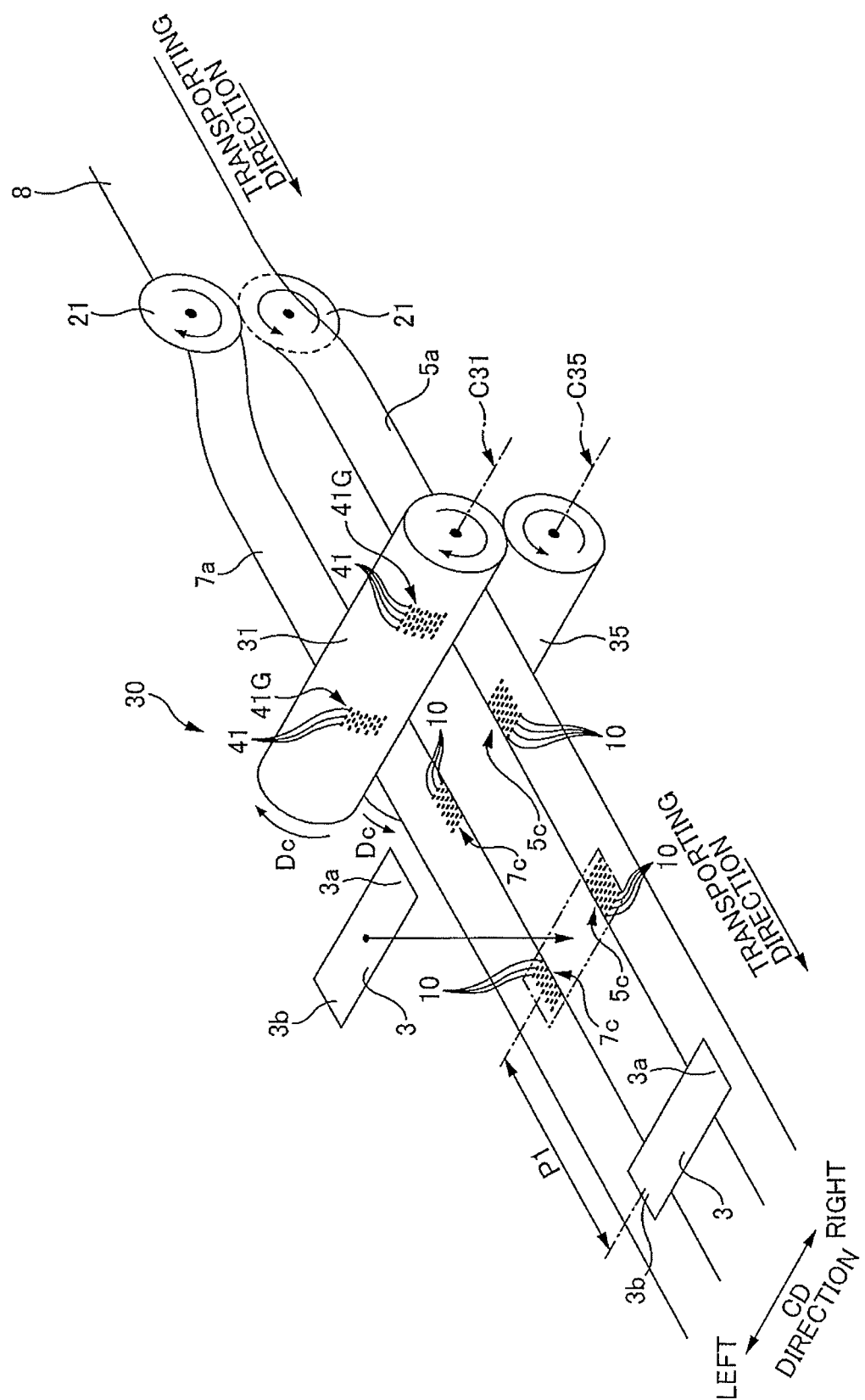
FIG. 5 is a perspective view of a step performed in a method of manufacturing of this embodiment.

FIG. 5 is a perspective view of a step handled in the method of manufacturing the sheet in this embodiment. In this step, the above-described slit processing is performed in product units of the diaper 1 in respect to both a continuous body of the skin side sheet 5a of the abdominal side strip member 5 and a continuous body of the skin side sheet 7a of the back side strip member 7, and thus elasticity of the regions 5c, 7c (hereinbelow, also referred to as joining target regions 5c, 7c) to which the front end portion 3a and the back end portion 3b of the above-described absorbent main body 3 are to be joined is weakened.

Therefore, the pair of skin side sheets 5a, 7a at the time of being supplied in this step is continuously transported, in a form of a continuous body along the transporting direction, and in a state aligned in the CD direction (a direction that intersects the transporting direction and that is also referred to as a left to right direction) with an interval therebetween. Note that, the transporting form in this step is a so-called horizontal flow, that is, the partially completed products of the diapers 1 are aligned with the width direction of the diaper 1 aligned in the transporting direction, and each partially completed product is transported in a state aligned with a predetermined pitch P1 in the transporting direction. Further, generation of the above-described pair of skin side sheets 5a, 7a is performed by dividing in two one continuous sheet 8 to the left and right in the CD direction by the discal rotating blade 21, while continuously transporting in the transporting direction the one continuous sheet 8 that is continuously let out from a reel device (not shown) in an upper step of this step.

As shown in FIG. 5, in this step a pair of the top and the bottom rolls 31, 35 for slit processing are installed. Each roll 31, 35 is opposed with the outer circumferential face to each other while directing the rotational axis directions C31, C35 in the CD direction. Then, the rolls are drivingly rotated in the circumferential direction Dc by an appropriate drive source such as a motor.

The outer circumferential face of the top roll 31 is provided with a pair of slit blade groups 41G, 41G (corresponds to protruding portion group) with multiple slit blades 41 (corresponds to protruding portions) arranged closely together, for example sandwiching the center of the top roll 31 in the CD direction. One of the slit blade group 41G is for performing a slit processing to the joining target region 5c of the skin side sheet 5a of the abdominal side strip member 5, and the other slit blade group 41G is for performing the slit processing to the joining target region 7c of the skin side sheet 7a of the back side strip member 7.

On the other hand, the bottom roll 35 is an anvil roll to receive the slit blade 41, that is, the outer circumferential face is formed as a smooth surface.

Therefore, when a pair of skin side sheets 5a, 7a are passed through between the top and the bottom rolls 31, 35 that drivingly rotate in the circumferential direction Dc, by each skin side sheet 5a, 7a being sandwiched with the slit blade groups 41G, 41G and the outer circumferential face of the bottom roll 35, the joining target regions 5c, 7c of each skin side sheet 5a, 7a are formed with multiple slits 10 cut through in the thickness direction.

By the way, in this lower step, a manufacturing step of the absorbent main body 3 joins in as shown in FIG. 5, and the absorbent main body 3 is put across between a pair of the skin side sheets to form a ladder like partially completed product (corresponds to a material). In other words, both end portions 3a, 3b of the absorbent main body 3 in the longitudinal direction are each joined to each joining target region 5c, 7c of the pair of the skin side sheets 5a, 7a.

Figure 7:
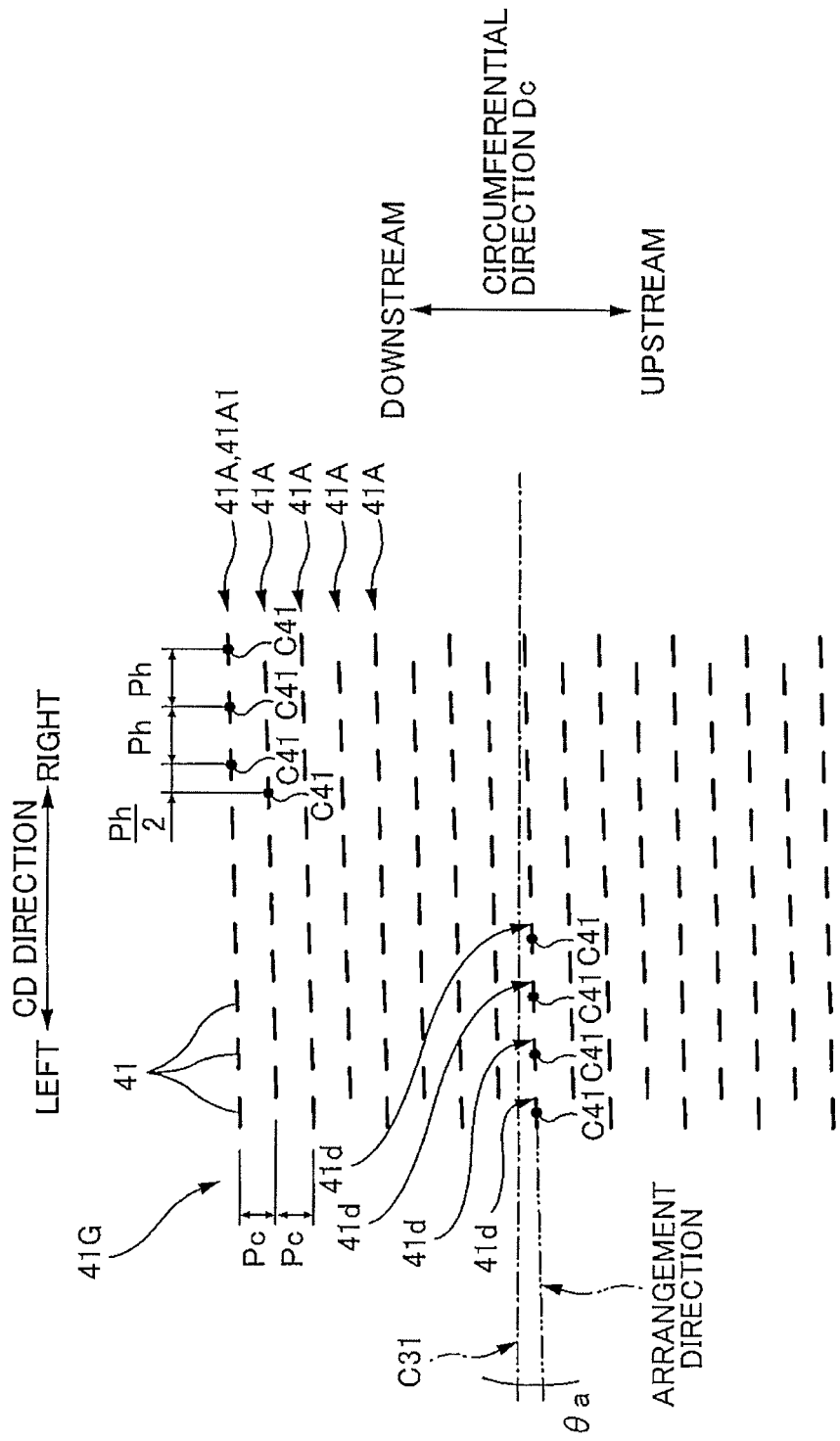
FIG. 7 is a diagram showing the right side slit blade group 41G of FIG. 6A opened on a plane.

FIG. 6A to FIG. 7 are explanatory diagrams of an arrangement pattern of the slit blades 41 of the slit blade groups 41G, 41G. FIG. 6A is a front view showing an appearance of the top roll 31, and FIG. 6B is a B-B cross section view in FIG. 6A. Further FIG. 7 is a diagram showing the right side slit blade group 41G opened on a flat surface.

In this example, as shown in FIG. 6A, the pair of slit blade groups 41G, 41G are different from each other in the number of blades they each have. Namely, the number of blades of the right side slit blade group 41G, is larger than that of the left side slit blade group 41G. The arrangement of the slit blades 41 in these pair of slit blade groups 41G, 41G, however, is basically made based on the arrangement pattern that is in a mirror image relationship to each other in regards to the central line CL in the CD direction. Thus, hereinbelow, the right side slit blade group 41G in FIG. 6A will be mainly described, and the description of the left side slit blade group 41G will be omitted.

As shown in FIG. 6A and FIG. 7, each slit blade 41 is a flat blade (linear blade) with the same shape and size as each other, in other words, the plane shape of the blade edge is linear. Further, the section shape of the blade is, as shown in FIG. 6B, a substantially triangular shape with the root side being wider than the blade edge side. Note that, the blade edge in this example is pointed in an acute angle with the blade edge angle a being 60°, but the blade edge may be beveled in a range in which the cutting property does not deteriorate.

As shown in FIG. 7, the outline of the slit blade group 41G is a substantially rectangular shape. Then, the arrangement pattern of the slit blade 41 is a so-called staggered arrangement. Namely, a plurality of the slit blade rows 41A (corresponds to protruding portion row) in which a plurality of slit blades 41, 41 . . . are aligned in a predetermined pitch Ph along the rotational axis direction C31 of the top roll 31 are configured provided in a predetermined pitch Pc in a circumferential direction Dc of the top roll 31, and each slit blade row 41A is shifted by just a half pitch (=Ph/2) in the rotational axis direction C31 in respect to a slit blade row 41A adjacent in the circumferential direction Dc. Further, the slit blades 41, 41 . . . belonging to the same slit blade row 41A are arranged so that a center C41 in each slit blade 41 is positioned on one line, and further the longitudinal direction of each slit blade 41 is also aligned in a direction of the line, and the appearance of each slit blade row 41A is in a straight dashed line.

The length of such a slit blade 41 in the longitudinal direction is selected from a range of, for example 3 to 5 mm. Further, the pitch Ph in the rotational axis direction C31 is selected from a range of for example 1 to 7 mm, in a range in which the adjacent slit blades 41, 41 do not connect to each other. Further, the pitch Pc in the circumferential direction Dc is selected from a range of, for example 2 to 8 mm. Then, by selecting each value from each of these ranges, the joining target region 5c (7c) of the sheet 5a (7a) becoming easy to tear due to the formed slits 10 can be effectively suppressed, while certainly weakening the elasticity in the region 5c (7c).

Here, as shown in FIG. 7, the arrangement direction (a direction formed by connecting the centers C41, C41 of each slit blade 41 belonging to the slit blade row 41A) of the slit blade row 41A is inclined in the circumferential direction Dc by only an inclined angle ea from the rotational axis direction C31 (refer to the chain double-dashed line). Thus, the position in the downstream end 41d in the circumferential direction Dc of the slit blades 41, 41 . . . configuring the same slit blade row 41A is shifted to the downstream side in the circumferential direction Dc subsequently, as it advances in one direction of the rotational axis direction C31.

Thus, the sandwiching timing of the sheet 5a (7a) by the downstream end 41d of the slit blade 41 can be made to be different for each of the slit blades 41, 41 and dispersed, therefore when the downstream end 41d of the slit blade 41 sandwiches the sheet 5a (7a), the counterforce that acts on the top roll 31 and the bottom roll 35 is alleviated. As a result, the rising of the top roll 31 is suppressed, and each slit blade 41 can certainly divide and cut through the sheet 5a (7a) part that the blade itself comes into contact.

Note that, this rising phenomenon is prone to occur particularly when starting dividing, in other words when the slit blade row 41A1 positioned most downstream in the circumferential direction Dc of the slit blade group 41G divides the sheet 5a (7a). Thus, by inclining the arrangement direction of the slit blade row 41A, for at least the most downstream slit blade row 41A1, the rising phenomenon is alleviated. Furthermore, if the position of the downstream end 41d of one slit blade 41 of the slit blades 41 belonging to the most downstream slit blade row 41A1 is shifted in the circumferential direction Dc from the downstream end 41d of another slit blade 41 belonging to the most downstream slit blade row 41A1, then a reasonable effect can be achieved, so that just one slit blade 41 may be shifted.

The inclined angle θa in regards to the arrangement of the slit blade row 41A is selected from an angle excluding 0° and 90°, and preferably selected from a range of 0.5° to 10°. If the angle is selected from this range, the plane shape of the joining target region 5c (7c) can be maintained in a substantially rectangular shape, and dispersion of the sandwiching timing can be certainly achieved. Note that, the reason that it is better for the plane shape of the joining target region 5c (7c) to be a rectangle than a parallelogram is because generally the shape of the end portions 3a, 3b in the longitudinal direction of the absorbent main body 3 is a rectangle (refer to for example FIG. 4).

By the way, by the dispersion of the above-described sandwiching timing, even in the case where only a constant total load can be added to the top and the bottom rolls 31, 35 when sandwiching, the load to be assigned for one slit blade 41 can be enlarged. As a result, each slit blade 41 can certainly divide and cut through the sheet 5a (7a) part that the blade itself comes into contact. The details are as follows.

Figure 8:
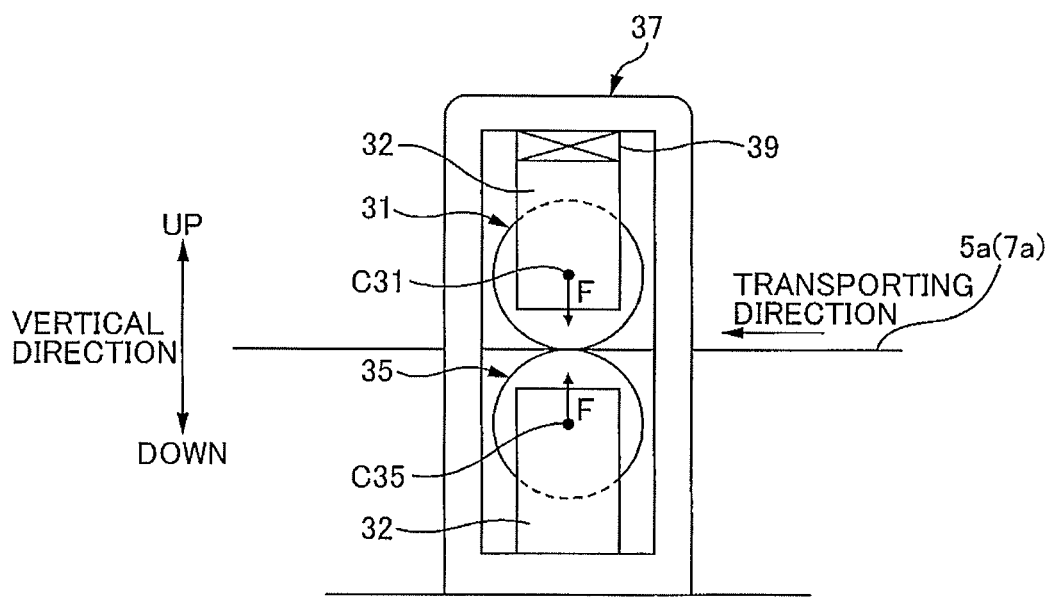
FIG. 8 is a side view of the top and bottom rolls 31, 35.

The top and bottom rolls 31, 35 are stored inside the case like housing 37 shown in the side view in FIG. 8. Then, via a hydraulic jack 39 arranged in between a chock 32 that supports both end portions of the top roll 31 and a chock 32 that supports both end portions of the bottom roll 35 and a housing 37, a vertical direction load F is added to the top and bottom rolls 31, 35 from the housing 37, and the vertical direction load F is applied for dividing of the slits 10 of the sheet 5a (7a). Then, generally, this vertical direction load F is a constant value. In this case, if the sandwiching timing of the plurality of slit blades 41, 41 . . . are different from each other and is dispersed, this vertical direction load F can be made to act in a concentrated manner on one slit blade 41 or a very small number of slit blades 41, and the dividing property of the slit blade 41 increases significantly. Then, as a result, each slit blade 41 can certainly divide and cut through the sheet 5a (7a) part that the blade itself comes into contact.

Figure 9:
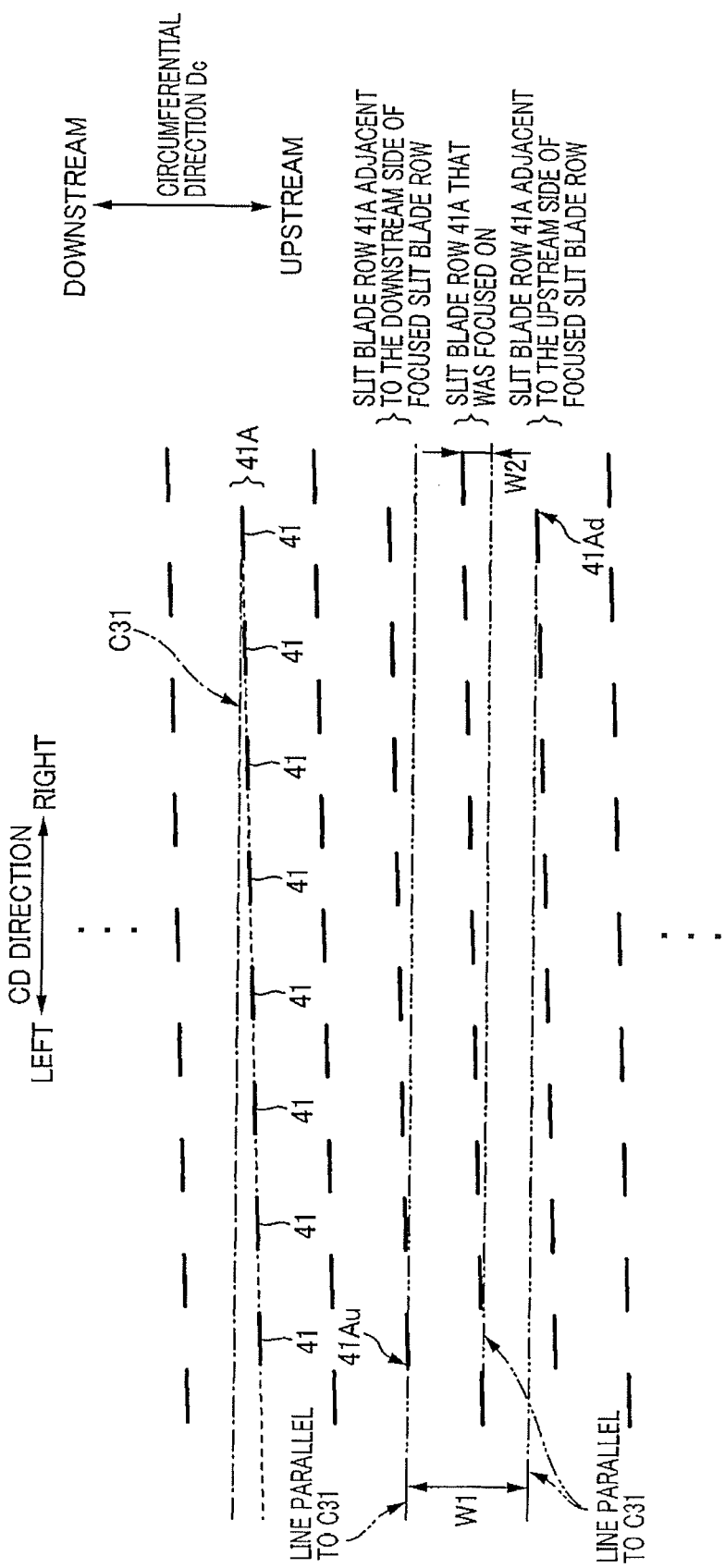
FIG. 9 is an enlarged diagram of an arrangement pattern of the right side slit blade group 41G.

In order to make such a sandwiching timing dispersion more reliable, as shown in a partially enlarged view of the arrangement pattern in FIG. 9, the slit blades 41, 41 belonging to the same slit blade row 41A may be arranged so as not to overlap each other in the circumferential direction Dc. In the illustrated example, each slit blade 41 belonging to the same slit blade row 41A is arranged on one line shown by a dotted line in FIG. 9, and the longitudinal direction of each slit blade 41 is facing the one line direction, and thus, overlap in the circumferential direction Dc can be completely avoided. By the way, in the above-described example in FIG. 7, this relationship is the best state established across all the slit blade rows 41A, 41A . . . of the slit blade group 41G, but this relationship may be established for at least one or more rows of the slit blade row 41A, and in that case a reasonable effect can be achieved.

Further, similarly in order to make dispersion of the sandwiching timing more certain, as shown in FIG. 9, the slit blade rows 41A, 41A . . . can be aligned so that the adjacent slit blade rows 41A, 41A do not overlap each other in the circumferential direction Dc. For example, in the illustrated example, an interval W1 in the circumferential direction between a downstream end 41Ad of an adjacent slit blade row 41A to the upstream side in the circumferential direction Dc of the focused slit blade row 41A and an upstream end 41Au of the adjacent slit blade row 41A to the downstream side in the circumferential direction Dc of the focused slit blade row 41A is wider than a dimension W2 of the focused slit blade row 41A in the circumferential direction Dc. As a result, overlap in the circumferential direction Dc can be avoided. By the way, in the above-described example in FIG. 7, this relationship is the best state established across all the slit blade rows 41A, 41A . . . of the slit blade group 41G, but the relationship can be established between at least an adjacent set of slit blade rows 41A, 41A, and in such a case a reasonable effect can also be achieved.

In order to make dispersion of the sandwiching timing more certain, as shown in FIG. 6A, the pair of the slit blade groups 41G, 41G may be aligned so that the slit blade 41 belonging to the right side slit blade group 41G of the left and right pair of the slit blade groups 41G, 41G and the slit blade 41 belonging to the left side slit blade group 41G do not overlap in respect to the circumferential direction Dc.

For example, in the example in FIG. 6A, overlapping within the slit blade row 41A is avoided as described above, and further overlapping between the slit blade rows 41A, 41A is also avoided. Then, in addition to this, the right side slit blade group 41G and the left side slit blade group 41G changes from a state in which the positions of the most downstream slit blade rows 41A1, 41A1 of each group are matched with each other in respect to the circumferential direction Dc to a state in which one slit blade group 41G is relatively moved entirely in the circumferential direction Dc by just a predetermined amount. Thus, the slit blade row 41A of the left side slit blade group 41G is fitted in the intervals between the slit blade rows 41A, 41A adjacent to each other of the right side slit blade group 41G.

By the way, as described above, the right side slit blade group 41G and the left side slit blade group 41G are arranged based on an arrangement pattern in which they are in a mirror image relationship with each other in respect to a central line CL of the top roll 31 in the CD direction (refer to FIG. 6A). Thus, when forming the slits 10 in the joining target regions 5c, 7c, the counterforce that acts on the top roll 31 and bottom roll 35 can be pressure distributed substantially symmetrically in respect to the central line CL, and as a result an asymmetric load in respect to the central line CL is not put on the sheets 5a, 7a or the rolls 31, 35, and therefore is superior in view of stability when cutting.

Figure 10:
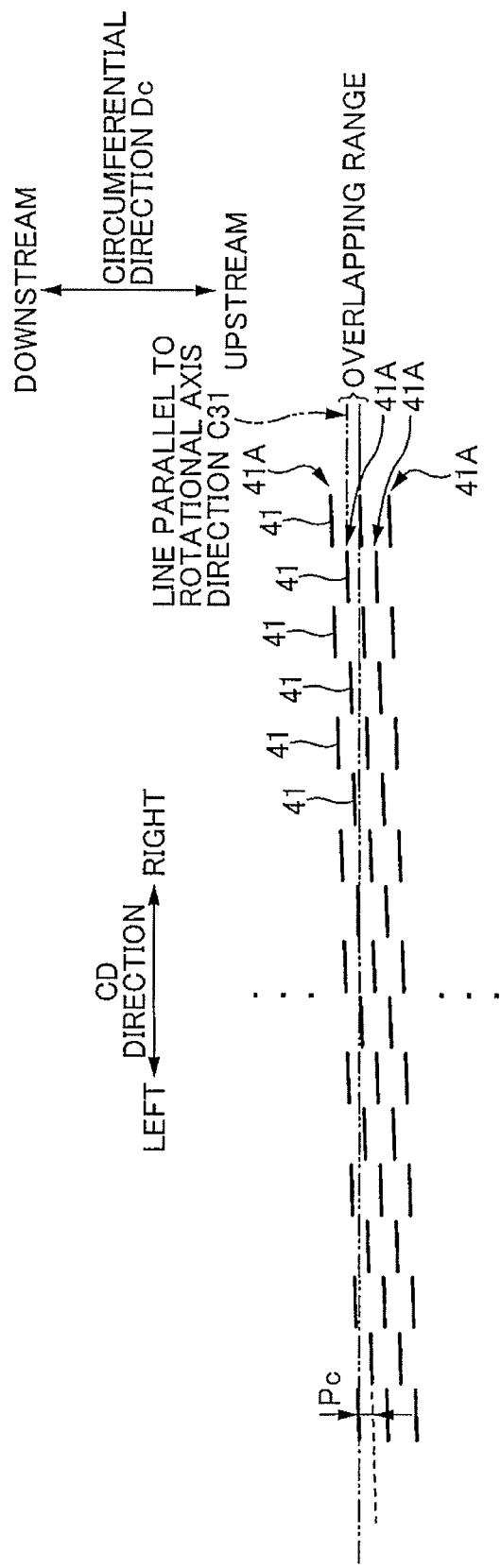
FIG. 10 is an explanatory diagram of a modified example of the arrangement pattern.
Figure 11:
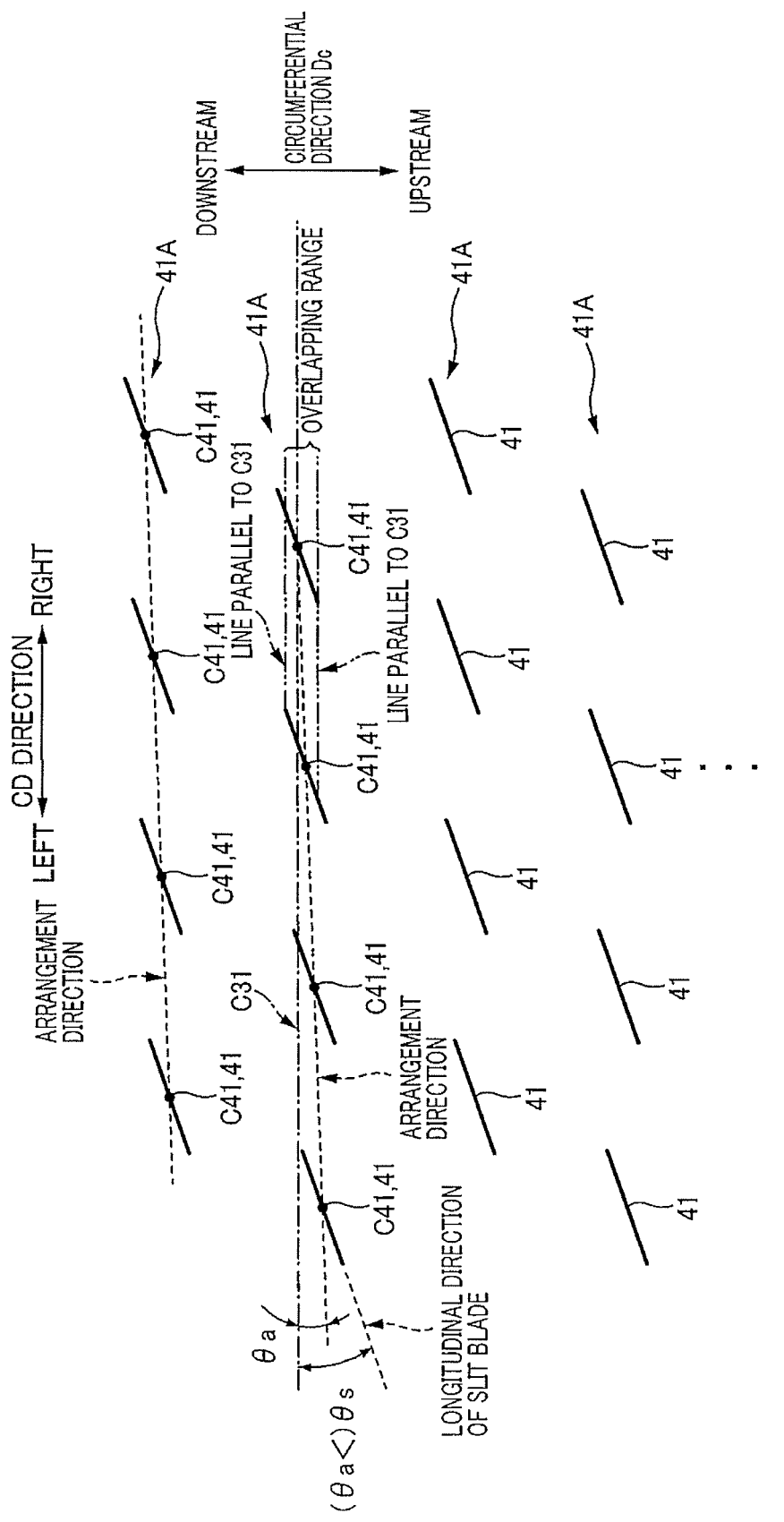
FIG. 11 is an explanatory diagram of another modified example of the arrangement pattern.
Figure 12:
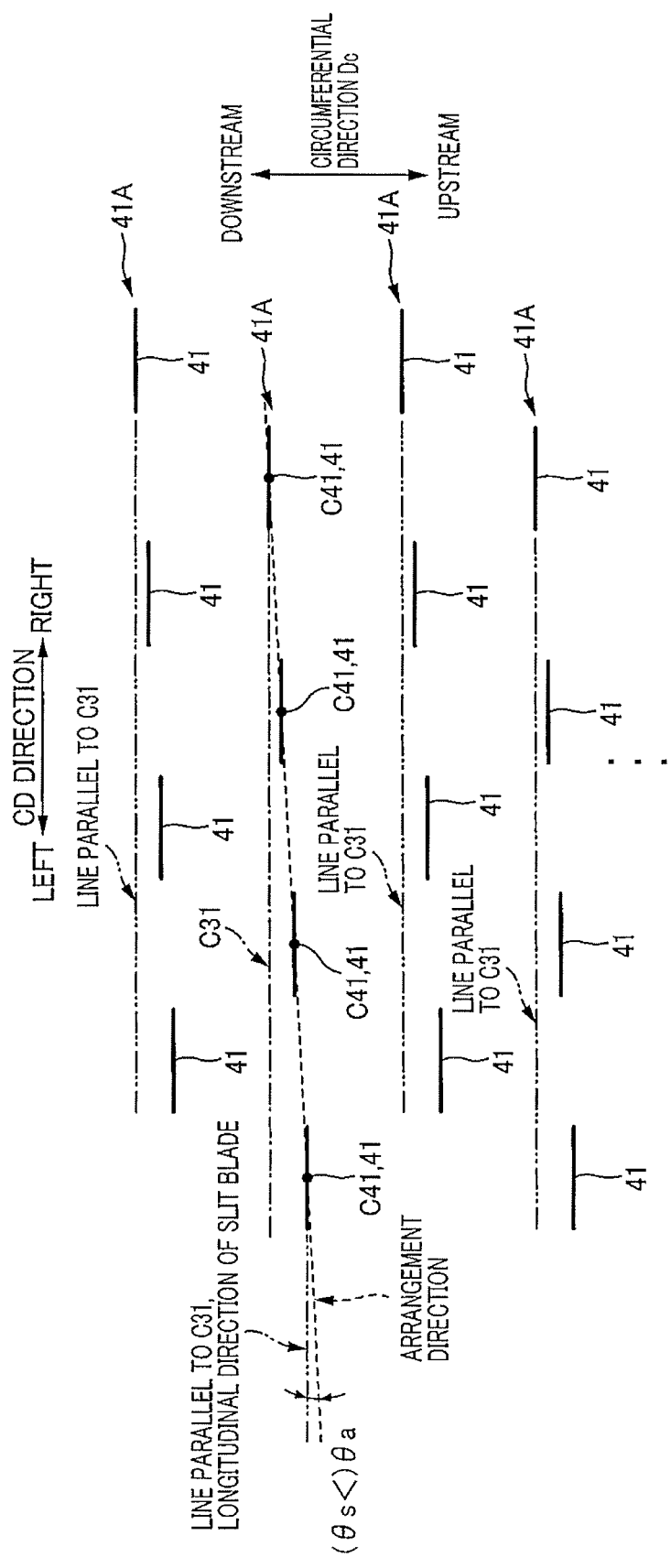
FIG. 12 is an explanatory diagram of yet another modified example of the arrangement pattern.

FIG. 10 to FIG. 12 are explanatory diagrams of modified examples of arrangement patterns, and one part is shown opened on a plane. Note that, the shape of the slit blade 41 is the same as the above-described embodiment.

The arrangement pattern example shown in FIG. 10 is different from the above-described embodiment in view of a pitch Pc in the circumferential direction Dc of the slit blade row 41A. Namely, the pitch Pc to align the plurality of slit blade rows 41A, 41A . . . in the circumferential direction Dc is made narrower than in the above-described embodiment, and therefore, the adjacent slit blade rows 41A, 41A are overlapped with each other in respect to the circumferential direction Dc.

The arrangement pattern examples shown in FIG. 11 and FIG. 12 are different from the above-described embodiment in view of an orientation in the longitudinal direction of the slit blades 41. Namely, in the above-described embodiment, as shown in FIG. 7 in a chain double-dashed line, the orientation in the longitudinal direction of the slit blades 41 match the arrangement direction of the slit blade row 41A, and thus all the slit blades 41 of the slit blade row 41A are on one line as a whole, but in the arrangement pattern in FIG. 11, the inclined angle θs of the slit blade 41 in the longitudinal direction from the rotational axis direction C31 is made larger than the inclined angle θa in the arrangement direction from the rotational axis direction C31, and the slit blades 41, 41 adjacent in the rotational axis direction C31 are overlapped with each other in respect to the circumferential direction Dc. Further, the arrangement pattern in FIG. 12 is, conversely, an example in which the inclined angle θs is smaller than the inclined angle θa, and in more detail is an example in which the longitudinal direction of the slit blade 41 is facing a direction parallel to the rotational axis direction C31. Such an inclined angle θs of the longitudinal direction of such a slit blade 41 is selected from an arbitrary angle other than 90°, and is preferably selected from a range of 0.5° to 5°. If the angle is selected from the latter range, the longitudinal direction of the slit blade 41 is substantially perpendicular to the transporting direction, and the joining target region 5c (7c) is divided with the slit blade 41 with multiple slits 10 along the CD direction, and thus the elasticity of the joining target region 5c (7c) in the transporting direction (the width direction in the diaper 1) is certainly weakened.

— other embodiment —

Hereinabove, the embodiments of the invention have been described, but the invention is not limited to these embodiments, and modifications shown hereinbelow are possible.

In the above-described embodiment, the sheet that has flexibility in the sheet itself was illustrated as the skin side sheets 5a, 7a, but it is not limited to this. For example, even if the flexibility of the sheet itself is small, a sheet added with flexibility by laying down and fastening an elastic member such as a rubber thread that has been extended may be used. In this case, in order to make the flexibility property in a joining target region of the sheet different from the surrounding sections, the elastic member in the joining target region is divided by the slit blades 41 in the slit blade group 41G.

Figure 13:
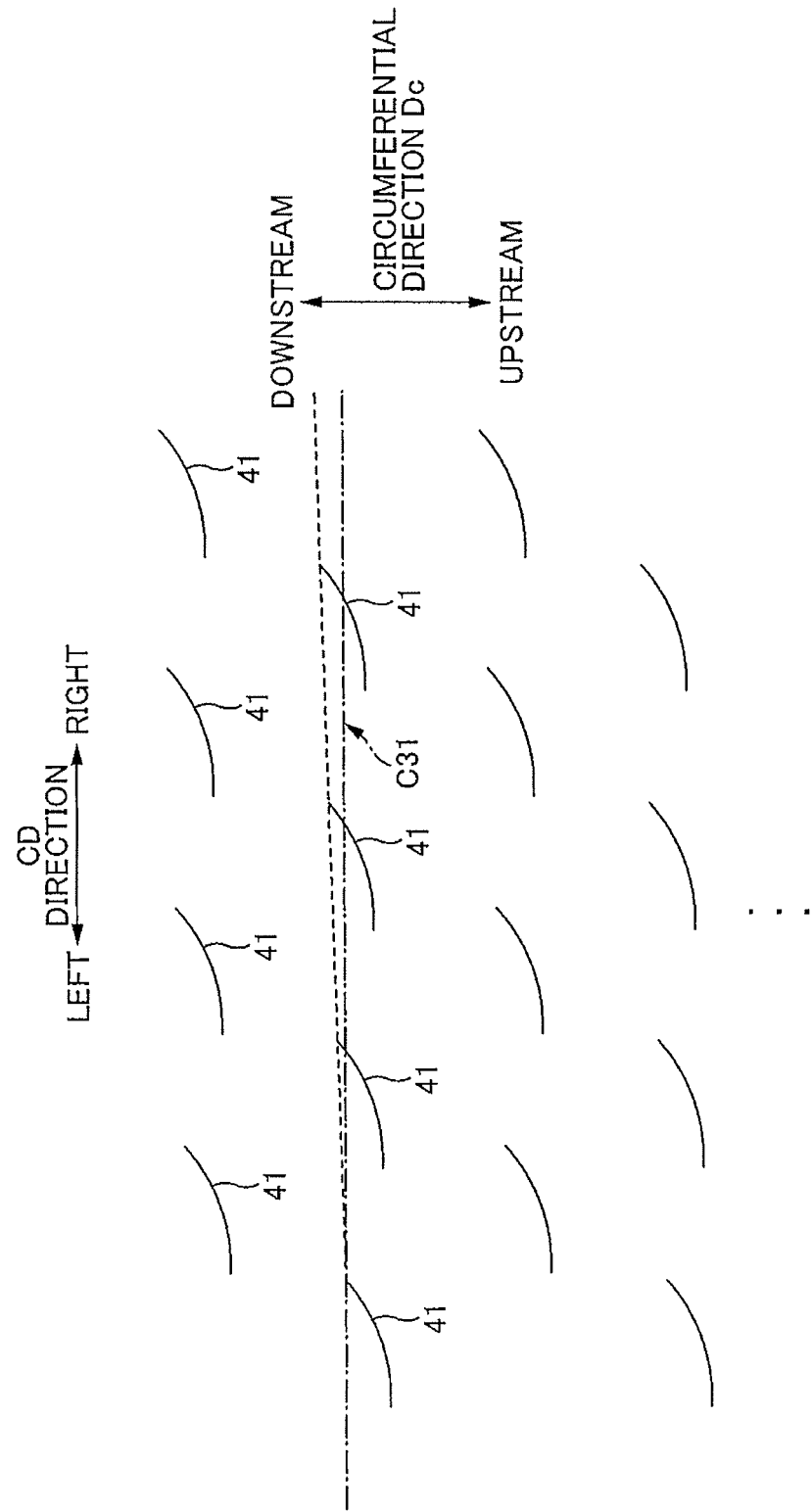
FIG. 13 is another embodiment of a planar view shape of a blade edge of the slit blade 41.

In the above-described embodiment, as one example of the protruding portion a flat blade like (linear blade like) slit blade 41 is illustrated, but it is not limited to the above. For example, as shown in FIG. 13, it may be a slit blade 41 that has a planar view shape of the blade edge curved in an arc shape. Further, the protruding portion is not limited to a cutter, and for example it may be an embossing protruding portion having a substantially flat top surface in a predetermined area. As the shape of the top surface of the embossing protruding portion, a rectangle, a rhombus, a circle and the like can be illustrated.

In the above-described embodiment, a staggered pattern is illustrated as an arrangement pattern of the slit blade 41 of the slit blade group 41G, but it is not limited to this, and for example it may be a lattice pattern (a grid pattern). In other words, it may be a pattern in which a center C41 of each slit blade 41 is not arranged in each intersection point of the lattice pattern.

In the above-described embodiment, as the skin side sheets 5a, 7a, the sheet added with flexibility by such as a gear drawing processing is illustrated, but it not limited to the above as long as it has flexibility. For example, a laminated sheet in which the sheet added with the flexibility is extended and a sheet with a lower flexibility than the sheet is overlapped and adhered may be used.

By the way, here as a supplemental description regarding the sheet added with flexibility by the gear drawing processing, first as one example of the raw material, a nonwoven fabric configured from an extensile fiber and a flexible fiber can be given. Then, the nonwoven fabric is passed through a pair of the top and the bottom gear rolls that rotate, and at that time the nonwoven fabric is extended in a rotating direction of the gear rolls with outer gear teeth of the top and the bottom gear rolls, and thus flexibility is developed in the nonwoven fabric.

Here, the flexible fiber refers to a fiber that is elastically extensile, and the extensile fiber refers to a fiber that is substantially non-elastically extensile. In other words, the extensile fiber can also be referred to as a fiber in which plastic deformation occurs with a smaller elongation than the elongation that is an elastic limit of the flexible fiber. As the extensile fiber, a thermoplastic polyolefin fiber can be illustrated, and further as a flexible fiber a thermoplastic elastomer fiber can be illustrated. The thermoplastic polyolefin fiber is, for example, a single fiber such as polypropylene fiber or polyester fiber, or a composite fiber with a core sheath structure made of a polypropylene or a polyester, and further the thermoplastic elastomer fiber is, for example a polyurethane fiber and the like.

Note that, the nonwoven fabric may be laminated in the thickness direction of the nonwoven fabric with, for example, a layer of only the extensile fiber and a layer of only the flexible fiber which are separated in layers.

Reference Signs List 1 disposable diaper (absorbent article), 1a waist opening, 1b around-leg opening, 3 absorbent main body,
3a front end portion, 3b back end portion, 3c absorbent body, 3d surface sheet, 3e back face sheet, 4 standing gather,
5 abdominal side strip member (abdominal side member),
5a skin side sheet (sheet), 5b outer side sheet,
5c joining target region, 5d region, 5e section,
6 elastic member, 7 back side strip member (back side member),
7a skin side sheet (sheet), 7b outer side sheet,
7c joining target region, 8 continuous sheet, 10 slit,
21 rotating blade, 30 manufacturing apparatus, 31 top roll, 32 chock,
35 bottom roll, 37 housing, 39 hydraulic jack,
41 slit blade (protruding portion), 41d downstream end of slit blade,
41A slit blade row (protruding portion row),
41Ad downstream end of slit blade row,
41Au upstream end of slit blade row,
41A1 most downstream slit blade row,
41G slit blade group (protruding portion group),
Dc circumferential direction, C31 rotational axis direction,
C41 center, C3 central portion, CL central line in CD direction,
P1 pitch, Pc pitch, Ph pitch, W1 interval, W2 dimension,

The invention claimed is:

1. A method of manufacturing a sheet formed, in a predetermined portion of the sheet, with a region having a different flexibility property, the sheet configuring an absorbent article, the method comprising:
rotating in a circumferential direction both a first roll formed with a protruding portion group in a predetermined area of an outer circumferential face and the second roll arranged with an outer circumferential face opposing the first roll,
forming, in the sheet, a region with the different flexibility property by passing the sheet in between the first roll and the second roll, and sandwiching the sheet with the protruding portion group and the outer circumferential face of the second roll,
wherein the protruding portion group has a plurality of rows of protruding portion rows with intervals therebetween in the circumferential direction, each of the protruding portion rows including a plurality of protruding portions inclined relative to a rotational axis of the first roll,
wherein a position of a downstream end in the circumferential direction of at least one protruding portion of the protruding portions configuring the protruding portion row positioned most downstream of the protruding portion group in the circumferential direction is shifted from a position of a downstream end of another protruding portion configuring the protruding portion row,
wherein the protruding portions in each of the protruding portion rows do not overlap each other in the circumferential direction,
wherein each of the protruding portions is a blade having a substantially triangular cross-section shape and an edge of the blade at a top of the substantially triangular cross-section shape is linear, and
wherein the protruding portions in the protruding portion rows adjacent to each other in the circumferential direction are not overlapped with each other in respect to the circumferential direction.

2. The method according to claim 1,
wherein the position of the downstream end in the circumferential direction of the protruding portion belonging to the protruding portion row positioned most downstream is subsequently shifted to an upstream side in the circumferential direction, as the position advances in one direction of the rotational axis.

3. The method according to claim 1,
wherein the position of the downstream end in the circumferential direction of the protruding portion belonging to each protruding portion row is subsequently shifted to the upstream side in the circumferential direction, as the position advances in one direction of the rotational axis.

4. The method according to claim 1,
wherein a longitudinal direction of the linear blade of each of the protruding portion is inclined by a predetermined angle other than 90° from the rotational axis of the first roll.

5. The method according to claim 1,
wherein a part of the sheet sandwiched between the protruding portion and the outer circumferential face of the second roll is divided in a thickness direction of the sheet.

6. The method according to claim 1,
wherein a pair of the protruding portion groups is provided and sandwich therebetween a center of the outer circumferential face of the first roll in the rotational axis of the first roll,
wherein the protruding portion of each of the pair of protruding portion groups are arranged in a predetermined arrangement pattern, and
wherein the arrangement pattern of one protruding portion group of the pair of protruding portion groups is a mirror image of the arrangement pattern of the other protruding portion group in respect to the center of the outer circumferential face of the first roll.

7. A method of manufacturing a sheet according to claim 6, wherein the protruding portion belonging to said one protruding portion group and the corresponding protruding portion belonging to the other protruding portion group are not overlapped with each other in respect to the circumferential direction.

8. The method according to claim 4, wherein the longitudinal directions of the linear blades of the protruding portions in each of the protruding portion rows coincide with each other.

9. The method according to claim 1, wherein
when the sheet is sandwiched between the protruding portion group of the first roll and the outer circumferential face of the second roll, a timing when the downstream end of said at least one protruding portion of the protruding portions configuring the protruding portion row positioned most downstream of the protruding portion group in the circumferential direction is in contact with the sheet is different from that when the downstream end of said another protruding portion configuring the protruding portion row is in contact with the sheet.

10. The method according to claim 1, wherein in each of the protruding portion rows, centers of the protruding portions are positioned on an imaginary straight line which is inclined with respect to the rotational axis.

11. The method according to claim 10, wherein
the protruding portions in each of the protruding portion rows are arranged in a first predetermined pitch in a direction of the rotational axis and in a second predetermined pitch in the circumferential direction, and
each of the protruding portion rows is shifted a half of the first predetermined pitch in the direction of the rotational axis in respect to an adjacent protruding portion row in the circumferential direction.

12. The method according to claim 11, wherein
the protruding portion group includes first, second and third protruding portion rows,
the second protruding portion row is adjacent to and arranged between the first and third protruding portion rows in the circumferential direction,
the first protruding portion row is upstream of the second protruding portion row in the circumferential direction,
the third protruding portion row is downstream of the second protruding portion row in the circumferential direction,
a distance in the circumferential direction between a downstream end of the first protruding portion row and an upstream end of the third protruding portion row is greater than a distance in the circumferential direction between a downstream end of the second protruding portion row and the rotational axis.

* * * * *